United States Patent
Hsu

(10) Patent No.: US 10,407,727 B2
(45) Date of Patent: Sep. 10, 2019

(54) **DONOR *KIR3DL1* AND *HLA-B* SUBTYPES AND LEUKEMIA CONTROL IN HLA-COMPATIBLE ALLOGENIC HEMATOPOIETIC STEM CELL TRANSPLANTATION**

(71) Applicant: MEMORIAL SLOAN-KETTERING CANCER CENTER, New York, NY (US)

(72) Inventor: Katharine Hsu, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 225 days.

(21) Appl. No.: 14/764,854

(22) PCT Filed: Jan. 30, 2014

(86) PCT No.: PCT/US2014/013896
§ 371 (c)(1),
(2) Date: Jul. 30, 2015

(87) PCT Pub. No.: WO2014/120949
PCT Pub. Date: Aug. 7, 2014

(65) Prior Publication Data
US 2015/0361506 A1 Dec. 17, 2015

Related U.S. Application Data

(60) Provisional application No. 61/758,558, filed on Jan. 30, 2013.

(51) Int. Cl.
| | |
|---|---|
| *C12Q 1/68* | (2018.01) |
| *C12P 19/34* | (2006.01) |
| *C12Q 1/6886* | (2018.01) |
| *C12Q 1/6881* | (2018.01) |
| *A61K 35/28* | (2015.01) |
| *C07H 21/02* | (2006.01) |
| *C07H 21/04* | (2006.01) |

(52) U.S. Cl.
CPC ............ *C12Q 1/6886* (2013.01); *A61K 35/28* (2013.01); *C12Q 1/6881* (2013.01); *C12Q 2600/106* (2013.01); *C12Q 2600/156* (2013.01); *C12Q 2600/172* (2013.01)

(58) Field of Classification Search
CPC .................. A61K 35/28; C12Q 1/6881; C12Q 2600/156; C12Q 2600/172
See application file for complete search history.

(56) References Cited

U.S. PATENT DOCUMENTS

2011/0129830 A1 6/2011 Ladner et al.

OTHER PUBLICATIONS

Giglio F. et al. Feb. 2012, vol. 18, Issue 2, Supplement, pp. S223-S224, Abstract 56.*
Hsu K.C. et al. J Immunol 2002; 169:5118-5129.*
Boulet S. et al. AIDS 2008, 22:1487-1491 (Year: 2008).*
Schmid, C. et al. Blood, Feb. 9, 2012, vol. 119, No. 6, pp. 1599-1606, Prepublished online as Blood First Edition paper, Dec. 13, 2011 (Year: 2011).*
International Search Report & Written Opinion, issued by the International Searching Authority (dated Apr. 29, 2014), for International Application No. PCT/US14/13896 (filed Jan. 30, 2014), 9 pgs.
Giglio; et al., "Donor KIR3DL1 and HLA-B Allotypes Control Leukemia Relapse After Allogeneic Hematopoietic Stem Cell Transplantation", In: 54th ASH Annual Meeting and Exposition (Dec. 8-11, 2012), Atlanta, GA, abstract 349, 4 pgs.
Martin; et al., "Innate partnership of HLA-B and KIR3DL1 subtypes against HIV-1", Nature Genetics (Jun. 2007), 39 (6):733-740.
Morvan; et al., "Phenotypic and Functional Analyses of KIR3DL1+ and KIR3DS1+ NK Cell Subsets Demonstrate Differential Regulation by Bw4 Molecules and Induced KIR3DS1 Expression on Stimulated NK Cells", The Journal of Immunology (Jun. 1, 2009), 182(11):6727-6735.
Trundley; et al., "Allelic expression patterns of KIR3DS1 and 3DL1 using the Z27 and DX9 antibodies", European Journal of Immunology (Mar. 2007), 37(3):780-787.

* cited by examiner

*Primary Examiner* — Stephen T Kapushoc
(74) *Attorney, Agent, or Firm* — Foley & Lardner LLP

(57) ABSTRACT

This disclosure generally relates to donor selection for hematopoietic stem cell transplantation. In particular, this disclosure relates to typing KIR3DL1 and HLA-B alleles as basis for donor selection.

16 Claims, 4 Drawing Sheets

DONOR KIR3DL1 AND HLA-B SUBTYPES AND LEUKEMIA CONTROL IN HLA-COMPATIBLE ALLOGENIC HEMATOPOIETIC STEM CELL TRANSPLANTATION

CROSS REFERENCE TO RELATED APPLICATION

This application claims the benefit of priority from U.S. Provisional Application No. 61/758,558, filed Jan. 30, 2013.

STATEMENT REGARDING FEDERALLY SPONSORED RESEARCH OR DEVELOPMENT

This invention was made with Government Support under HL088134, AI069197 and CA023766 awarded by the National Institutes of Health. The Government has certain rights in this invention.

FIELD OF THE DISCLOSURE

This disclosure generally relates to donor selection for hematopoietic stem cell transplantation. In particular, this disclosure relates to typing KIR3DL1 and HLA-B alleles as basis for donor selection.

BACKGROUND ART

Natural killer (NK) cells play an important innate immune role in controlling viral infection and malignancy. An increasing understanding of how NK immunogenetics control NK function has led to important associations between NK immunogenetics and disease outcomes. The most widely studied family of genes controlling human NK cell response is the polymorphic killer immunoglobulin-like receptor (KIR) gene family, with wide inter-individual variability based on differences in gene content and allelic polymorphism[1]. Recognition of self-specific HLA class I molecules on autologous cells by inhibitory KIR leads to NK cell inhibition. Conversely, non-engagement of the inhibitory KIR by target cells with reduced class I expression permits NK activation through simultaneous stimulatory signaling. Furthermore, interaction between self-specific inhibitory MR and cognate HLA ligands is also fundamental to NK "education"[2], in which cells expressing inhibitory KIR for self-HLA are "licensed" and have higher capacity for response compared to "unlicensed" NK cells which lack inhibitory KIR for self-HLA[3,4]. Under inflammatory conditions, however, unlicensed NK cells can be stimulated to exhibit higher effector function[2,5,6].

In hematopoietic cell transplantation (HCT), NK alloreactivity and leukemic control can occur through the stimulation of unlicensed NK cells lacking inhibitory KIR for self-HLA molecules[7-9].

The KIR3DL1/S1 gene locus is one of the oldest and most polymorphic loci of the KIR gene family and is the only locus whose alleles encode for both inhibitory (KIR3DL1) and activating (KIR3DS1) receptors[10]. Although the ligand for the activating KIR3DS1 allotype remains unknown[11,12], the ligands for the numerous inhibitory KIR3DL1 allotypes are the polymorphic HLA-B molecules characterized by the Bw4 motif at positions 77-83[13], with dimorphism between isoleucine or threonine at position 80 (Bw4-I$^{80}$ vs Bw4-T$^{80}$) important for differences in inhibitory response upon interaction with KIR3DL1 allotypes[14,15]. KIR3DL1 alleles are expressed at different densities, and their inhibitory activities are closely proportional to their abundance on the NK cell surface[14-18]. This variability has been translated into an operative grouping system: high-expression (KIR3DL1*h), low-expression (KIR3DL1*l) and null subtypes with no surface expression (KIR3DL1*n). Among the groups, there are known dichotomies in inhibitory response to the Bw4-I$^{80}$ and Bw4-T$^{80}$ subtypes, with some evidence linking highly inhibitory interactions to higher NK function[14,19]. In patients infected with human immunodeficiency virus (HIV), KIR3DL1/Bw4 allele combinations predictive of highly inhibitory interactions and especially those involving B*57 and B*2705, are associated with stronger protection from HIV progression compared to weak inhibition combinations[20,21]. The association of strong inhibitory combinations with protection from AIDS progression may reflect the greater efficiency of highly educated NK cells at clearing the infected target cell, whose class I expression is down-regulated by the HIV Nef protein[19,22-24].

In allogeneic HCT, where differences in HLA alleles between the stem cell donor and patient markedly influence transplant outcome, the role of KIR alleles, particularly in the context of differentially inhibiting class I ligand alleles, is unknown.

SUMMARY OF THE DISCLOSURE

The inventors evaluated the effects of KIR3DL1/HLA-Bw4 subtype combinations with known differences in strengths of inhibition/interaction on transplant outcomes in leukemia patients receiving an HLA-compatible stem cell allograft from an unrelated donor (URD). The data show that donor KIR3DL1 and donor-recipient HLA-Bw4 allele combinations predictive of weak NK inhibition in the patient are associated with improved leukemia control and superior survival following HCT compared to combinations predictive of strong inhibitory interactions. These findings illuminate inhibitory capacity as a significant dimension controlling anti-tumor NK activity in allogeneic HLA-matched HCT and highlight the importance of identifying donor KIR subtypes to protect patients from leukemic relapse following allogeneic HCT.

Accordingly, this disclosure provides methods for improved donor selection for hematopoietic stem cell transplantation for leukemia based on typing KIR3DL1 and HLA-B alleles in candidate donors and selecting donors with desirable KIR3DL1 alleles in combination with donor-recipient HLA-B alleles.

DETAILED DESCRIPTION

Figure 1A:
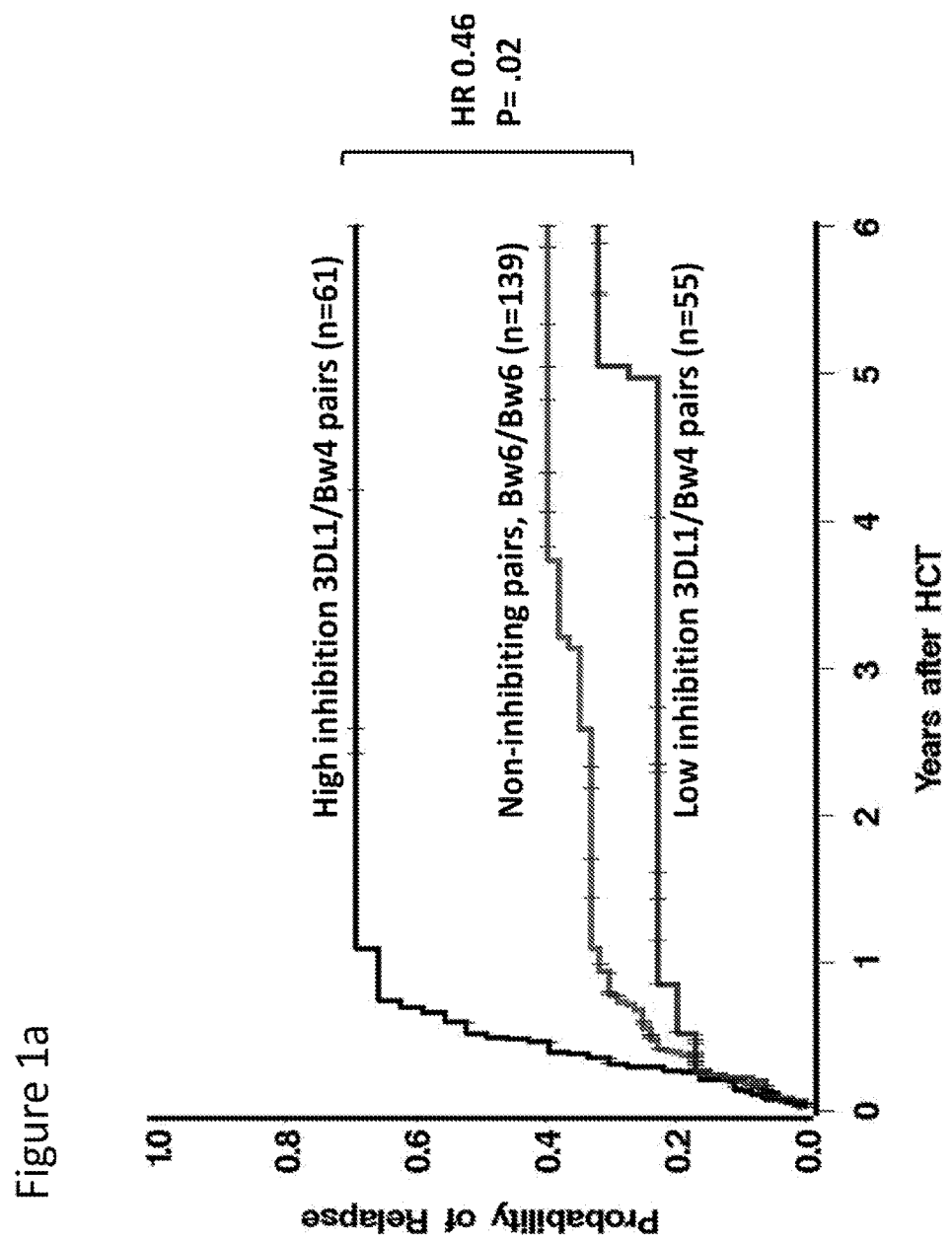
FIG. 1. Donor KIR3DL1/HLA-Bw4 subtype pairs associated with weak inhibitory interactions are protective from relapse in AML patients following HCT. Among donors with KIR3DL1-H subtypes, those with Bw4-T$^{80}$ (weak interaction) are associated with lower relapse compared to those with Bw4-I$^{80}$ (strong interaction) in AML patients after HCT. Among donors with 3DL1-L subtypes, those with Bw4-I$^{80}$ (weak interaction) are associated with lower relapse in AML patients after HCT, compared to those with Bw4-T$^{80}$ (strong interaction). (a) Combined, 3DL1-Bw4 allelic combinations with weak inhibitory interaction are associated with lower relapse compared to combinations with strong inhibitory interaction. Bw6/Bw6 donors are also associated with lower relapse compared to strong inhibitory combinations. (b) Donors with high inhibitory interactions further subdivided into those with 3DL1-H with HLA-B*2705 or B*57 are associated with the highest relapse rate compared to donors with 3DL1-H+non-B*2705 or non-B*57 alleles and compared with other HLA-B subtype groups.

For patients undergoing allogeneic HCT, donor preference is given to those matched for up to 12 HLA alleles[36,37]. While GvHD and graft rejection have decreased due to tighter HLA matching, risks of leukemic relapse and overall mortality remain disappointingly high. It has been shown herein that donor KIR3DL1 and HLA-Bw4 allele combinations with low inhibitory interactions were associated with lower AML relapse and higher survival, and, were not associated with a higher risk for GvHD. Conversely, high inhibitory combinations and, in particular, combinations with B*2705 and B*57 were associated with progressively higher relapse risk and lower survival. Nearly all (99%) patients exhibited the same HLA-B epitopes (Bw6, Bw4-T$^{80}$, Bw4-I$^{80}$) as their donors, indicating that even in HLA-matched allogeneic HCT, epistatic interactions between donor KIR and HLA class I at the allotype resolution can have a profound impact on transplant outcome.

The findings disclosed herein confirm a key role of interaction between 3DL1 and HLA-B allotypes in determining HCT outcomes, providing valuable insight to inhibitory controls of NK effects in an HLA-matched setting. The findings support KIR3DL1 allele typing to select stem cell donors with favorable KIR-HLA allelic combinations to minimize inhibition, maximize leukemic toxicity, lower relapse rates and increase survival. Considering the high frequencies of both HLA-Bw4 and KIR3DL1 in the population (70% and 95%, respectively)[46], selection of a donor with advantageous KIR3DL1 alleles is highly relevant and feasible in clinical practice, where genetic selection criteria currently focus solely on HLA allele-matching.

In one aspect, this disclosure provides a method of selecting a hemotopoietic cell donor for allogeneic hemotopoietic cell transplantation (HCT) to an acute myelogenous leukemia (AML) patient.

In some embodiments, the patient requiring HCT expresses HLA-Bw4. Typically, for a patient requiring HCT, more than one donor is identified. Thus, for a given patient, potential donors, equivalent based on HLA-matching, would be screened in accordance with the method disclosed herein in order to select the best donor based on donor and recipient KIR3DL1 and HLA-Bw4 allele combinations.

In accordance with the present method, a genomic DNA-containing sample is obtained from a candidate donor matched for HLA-Bw4. The sample can be a tissue or blood sample, including, but not limited to, blood, fractions of blood, peripheral blood cells, skin or tissue biopsies, buccal swab samples, and umbilical cord blood. In some embodiments, the sample is processed to permit allele typing, e.g., a cell-containing fraction is obtained from the sample, and genomic DNA is isolated. In other embodiments, a sample is used directly in allele typing.

The genomic DNA from the sample, processed or otherwise, is then analyzed to determine whether the KIR3DL1 gene is present (96% of individuals), and which allele(s), KIR3DL1-h, KIR3DL1-l, KIR3DL1-n, or KIR-3DS1, is present; i.e., allele typing of the KIR3DL1 gene. Allele typing of the KIR3DL1 gene is achieved by using various approaches described in the art, including, but not limited to, hybridization based on sequence-specific oligonucleotides, sequencing, PCR-SSP ("sequence-specific primer"), and combinations thereof.

A "KIR3DL1-h", as used herein, refers to an allele which expresses the KIR3DL1 receptor at high densities on the cell surface of NK cells detectable by cell surface staining, or an allele which is yet to be characterized for surface staining but shares substantial sequence similarity to an allele which expresses the KIR3DL1 receptor at high densities on the cell surface of NK cells detectable by cell surface staining. By "substantial sequence similarity", it is meant that the relevant sequences share at least about 90%, 95%, 98%, 99% or higher identity at the nucleotide level, or at least about 90%, 95%, 98%, 99% or higher similarity or identity at the amino acid level.

Cell surface staining can be performed using an antibody directed to KIR3DL1 receptor. Examples of suitable antibodies include Z27 or DX9, both widely available, for example, from BD Biosciences (San Jose, Calif.) or ThermoFisher Scientific (Waltham, Mass.).

KIR3DL1-h alleles are those alleles which have been characterized by cell surface staining, including but not limited to KIR3DL1*001, *002, *008, *015, *020, *033, and *052. Alleles yet to be characterized for surface staining but which share substantial sequence similarity to a KIR3DL1-h allele characterized by high density cell surface staining include but are not limited to *009, *016, *043, *067, *026, *052, *034, *035, *022, *017, *066, *029, *038, *025, *054, *018, *051, *023, *028, *062, *030, *024N, *031, *059, *060, *061, *064, *065, *074, *075, *076, *077, and *057.

A "KIR3DL1-l", as used herein, refers to an allele which expresses the KIR3DL1 receptor at low densities on the cell surface of NK cells detectable by cell surface staining (e.g., using Z27 or DX9), or an allele which is yet to be characterized for surface staining but shares substantial sequence similarity to an allele which expresses the KIR3DL1 receptor at low densities on the cell surface of NK cells detectable by cell surface staining.

KIR3DL1-l alleles which have been characterized by cell surface staining include but are not limited to KIR3DL1*005, *007, and *053. Alleles yet to be characterized for surface staining but which share substantial sequence similarity to a KIR3DL1-l allele characterized by low density cell surface staining include but not limited to *032, *033, *068, *044, and *041.

A "KIR3DL1-n", as used herein, refers to an allele which expresses KIR3DL1 molecules retained intracellularly and not detectable by cell surface staining (e.g., using Z27 or DX9). KIR3DL1-n alleles include but are not limited to *004, *019, and *056. Alleles yet to be characterized for surface staining but which share substantial sequence similarity to a KIR3DL1-n allele characterized by low density cell surface staining include but not limited to *021, *036, *037, *039, *056, *072, *063, and *040.

A KIR3DS1 allele expresses KIR3DS1 molecules, detectable by surface staining with Z27 but not DX9. KIR3DS1 alleles include but are not limited to KIR3DS1*013, *047, *010, *011, *012, *014, *045, *046, *048, *049N, *050, *055, and *058.

Once the KIR3DL1 allele typing information is obtained, the donor can be assigned to one of the following subtype groups based on its allele combination: KIR3DL1-H (KIR3DL1*h/*h, or KIR3DL1*h/KIR3DS1), KIR3DL1-L (KIR3DL1*l/*l, KIR3DL1*l/*h, or KIR3DL1*l/KIR3DS1), or KIR3DL1-N (KIR3DL1*n/*n, KIR3DL1*n/*h, KIR3DL1*n/*l, or KIR3DL1*n/KIR3DS1).

One can then determine the inhibition potential of the donor KIR3DL1 subtype and the HLA-Bw4 allele combination, wherein the combinations of KIR3DL1-L and HLA-Bw4-I80, and KIR3DL1-H and HLA-Bw4-T80 represent low inhibitory combinations, the combinations of KIR3DL1-L and HLA-Bw4-T80, and KIR3DL1-H and HLA-Bw4-I80 represent high inhibitory combinations, and where HLA-B*57 and B*2705 are highly inhibitory Bw4 alleles in specific combinations with KIR3DL1 HLA-B*2705 is a Bw4-T80 allele but appears to have a highly inhibitory relationship with 3DL1-H. For purposes of this determination, donors are considered Bw4-I$^{80}$, Bw4-T$^{80}$, or Bw4-negative (Bw6/Bw6). All donors positive for Bw4-I$^{80}$, homozygous or heterozygous, are considered in the Bw4-I$^{80}$ group, independent of the presence/absence of HLA-Bw4-T$^{80}$.

A donor can be selected on the basis that the donor and recipient genotypes provide a low inhibitory combination of donor KIR3DL1 and donor/recipient HLA-Bw4 alleles. Such donor is associated with a reduced risk of AML relapse and increased rate of survival in the AML recipient.

The present description is further illustrated by the following examples, which should not be construed as limiting in any way. The contents of all cited references (including literature references, issued patents, and published patent applications as cited throughout this application) are hereby expressly incorporated by reference.

EXAMPLE

In experiments described in this Example, we tested the hypothesis that differences in KIR3DL1-mediated NK inhibition by HLA-Bw4 subtypes can influence donor NK activity against leukemia in hematopoietic stem cell transplantation (HCT). Among 299 patients with acute myelogenous leukemia (AML) who received HLA-compatible HCT, allelic combinations of donor KIR3DL1 and HLA-Bw4 predictive of low inhibitory interactions were strongly and consistently associated with lower relapse and improved survival. These data are the first to demonstrate the importance of allotypic KIR-HLA interactions in leukemic control and indicate that NK cells with lower capacity for inhibition have the most potent anti-leukemic effects. Considering the high frequencies of HLA-Bw4 and KIR3DL1 among patients and donors, consideration of KIR3DL1 allele typing for stem cell donor selection is feasible and may provide better disease control for AML patients undergoing allogeneic HCT.

Results

Impact of Donor KIR3DL1 or HLA-Bw4 Allele Groups on Allogeneic HCT

We evaluated donor KIR3DL1 and HLA-Bw4 alleles for 299 AML patients who received an allogeneic HCT from an HLA-compatible donor (Table 1). Patients and donors were matched for 10 HLA alleles in 78.9%, and matched for HLA-B alleles in 94.6%. All but 3 donor-patient pairs were matched for HLA-B subtype (Table 1).

There were no statistically significant associations of donor HLA-Bw4 subtype, segregated into Bw4-I$^{80}$ and Bw4-T$^{80}$ subtypes, on the outcomes of overall mortality (OM), non-relapse mortality (NRM), relapse, and acute graft-versus-host disease (GvHD) among all patients and among AML versus MDS/CML patients (data not shown). Patients homozygous for HLA-Bw6 alleles (Bw6/Bw6) and therefore lacking the Bw4 epitope, represented 41% of patients. When AML patients were segregated according to absence or presence of Bw4 (Bw6/Bw6 vs Bw4/Bw4 or Bw4/Bw6), there was no statistically significant reduction in relapse (HR 0.83, p=0.45).

Among donors, 95.5% possessed the KIR3DL1 gene. Allele typing successfully assigned alleles to all KIR3DL1-positive donors and identified three new alleles: KIR3DL1*00403 (GenBank accession number GU063854); KIR3DL1*072 (GenBank accession number GU063855) and KIR3DL1*073 (GenBank accession number GU063857). Frequencies of KIR3DL1*h, KIR3DL1*l and KIR3DL1*n alleles were 64.6%, 29.3% and 27.9%, respectively (Table 1). Of the 17 different KIR3DL1 alleles identified, 4 had frequencies higher than 20% (*001, *002, *004 and *005), consistent with published data[30], and 10 had frequencies less than 5%. Donors were segregated by KIR3DL1 alleles into functionally relevant groups similar to published criteria[20]: donors with only high-expressing KIR3DL1 alleles comprised group 3DL1-H (KIR3DL1*h/*h, KIR3DL1*h/KIR3DS1); donors with at least one low-expressing KIR3DL1 allele comprised group 3DL1-L (KIR3DL1*l/*l, KIR3DL1*l/*h, KIR3DL1*l/KIR3DS1); and donors with at least one null allele comprised group 3DL1-N (KIR3DL1*n/*n, KIR3DL1*n/*h, KIR3DL1*n/*l, KIR3DL1*n/KIR3DS1). Among donors, frequencies of 3DL1-H, 3DL1-L, and 3DL1-N were 43%, 27%, and 29%, respectively (Table 1). Four donors could not be assigned to a group due to lack of information regarding expression of their KIR3DL1 alleles and were therefore not included in the analysis. No group (3DL1-H, 3DL1-L or 3DL1-N) was significantly associated with differences in HCT outcome from the others, regardless of disease category (data not shown).

Weak Inhibitory Donor 3DL1-H and Bw4-I$^{80}$ Combinations are Associated with Lower AML Relapse Following HCT We then considered KIR3DL1 groups in combination with cognate HLA-Bw4 ligand subtypes on HCT outcomes, segregating combinations according to strong or weak inhibition combinations and comparing to Bw6/Bw6 individuals. All results are adjusted for disease status. Among AML patients with a 3DL1-H donor, those whose donor exhibited the weak inhibitory combination 3DL1-H+Bw4-T$^{80}$ experienced lower relapse when compared to those with the highly inhibitory 3DL1-H+Bw4-I$^{80}$ combination (HR 0.47; P=0.099). Patients with Bw6/Bw6 donors also had lower relapse compared to patients transplanted from donors with strong inhibition subtype combinations (HR 0.7; P=0.33).

Inhibitory Donor 3DL1-H and Bw4-B*2705 or Bw4-B*57 Combinations are Associated with Highest AML Relapse Following HCT HLA-B*2705 and B*57 alleles are known to have particularly high protective effect against HIV[20,31], likely related to higher NK functional capacity via interaction with KIR3DL1[19,23]. To determine if these alleles specifically enhance risk for relapse, we divided 3DL1-H donors with B*57 or B*2705 or non-B*57 Bw4-I$^{80}$ alleles. The protection from relapse seen in the weakly inhibitory group (3DL1-H+Bw4-T$^{80}$) relative to the highly inhibitory group was even more striking when the highly inhibitory group was restricted to those with B*2705 or B*57 (HR 0.3; P=0.02). These data support a model where licensed but weakly inhibited NK cells are most effective at controlling leukemia. In contrast, NK cells that are more inhibitable, despite being highly licensed, are less effective at tumor clearance.

Weak Inhibitory Donor KIR3DL1-L and Bw4 Allele Combinations are Associated with Lower AML Relapse In contrast to the 3DL1-H group, we found that among 3DL1-L donors, those with the weak inhibitory 3DL1-L+HLA-Bw4-$I^{80}$ combination were associated with lower AML, relapse in the patient when compared to donors with the highly inhibitory 3DL1-L+Bw4-$T^{80}$ combinations (HR 0.47; P=0.2). Patients transplanted from a 3DL1-L, Bw6/Bw6 donor also had a lower rate of relapse compared to patients transplanted from KIR3DL1-L+Bw4-$I^{80}$ donors (HR 0.6; p=0.3).

Figure 1B:
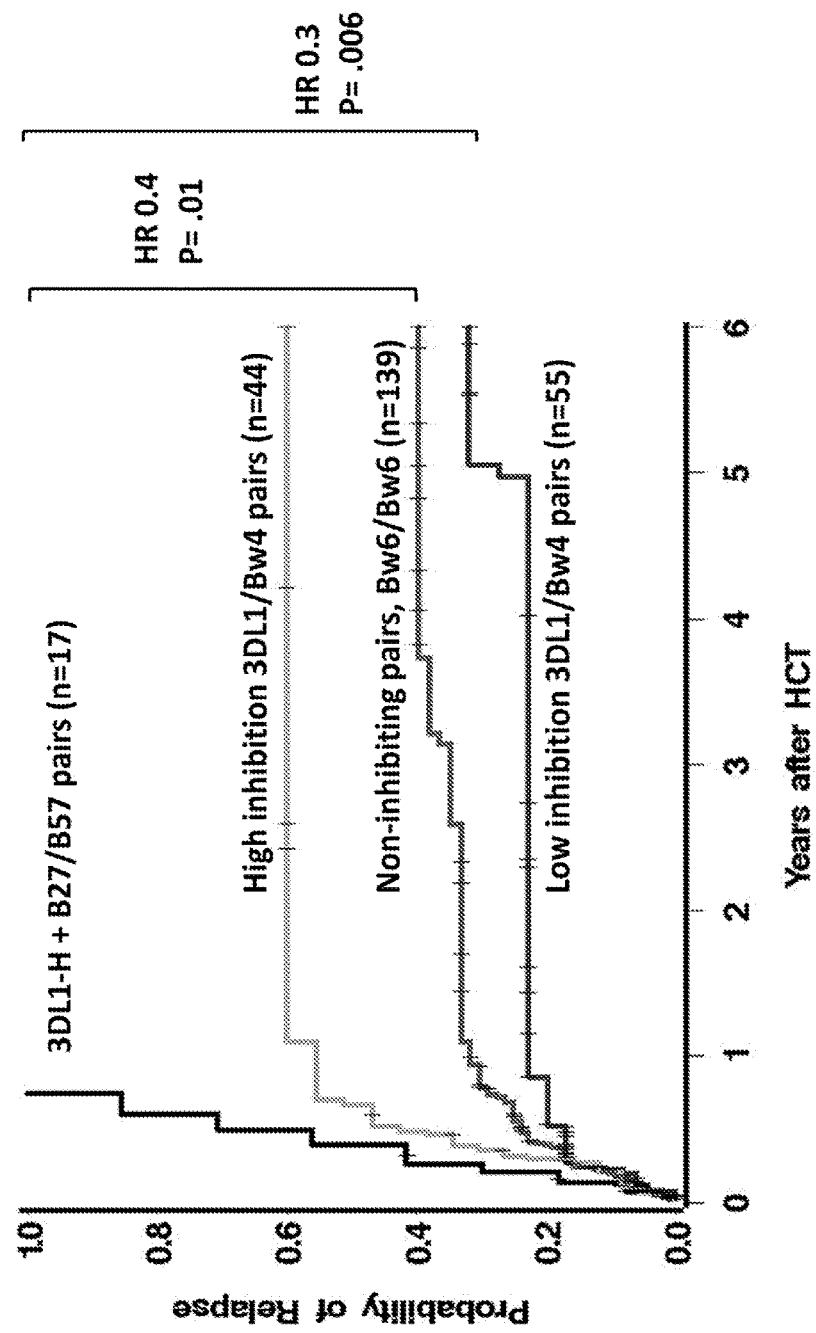
Figure 2:
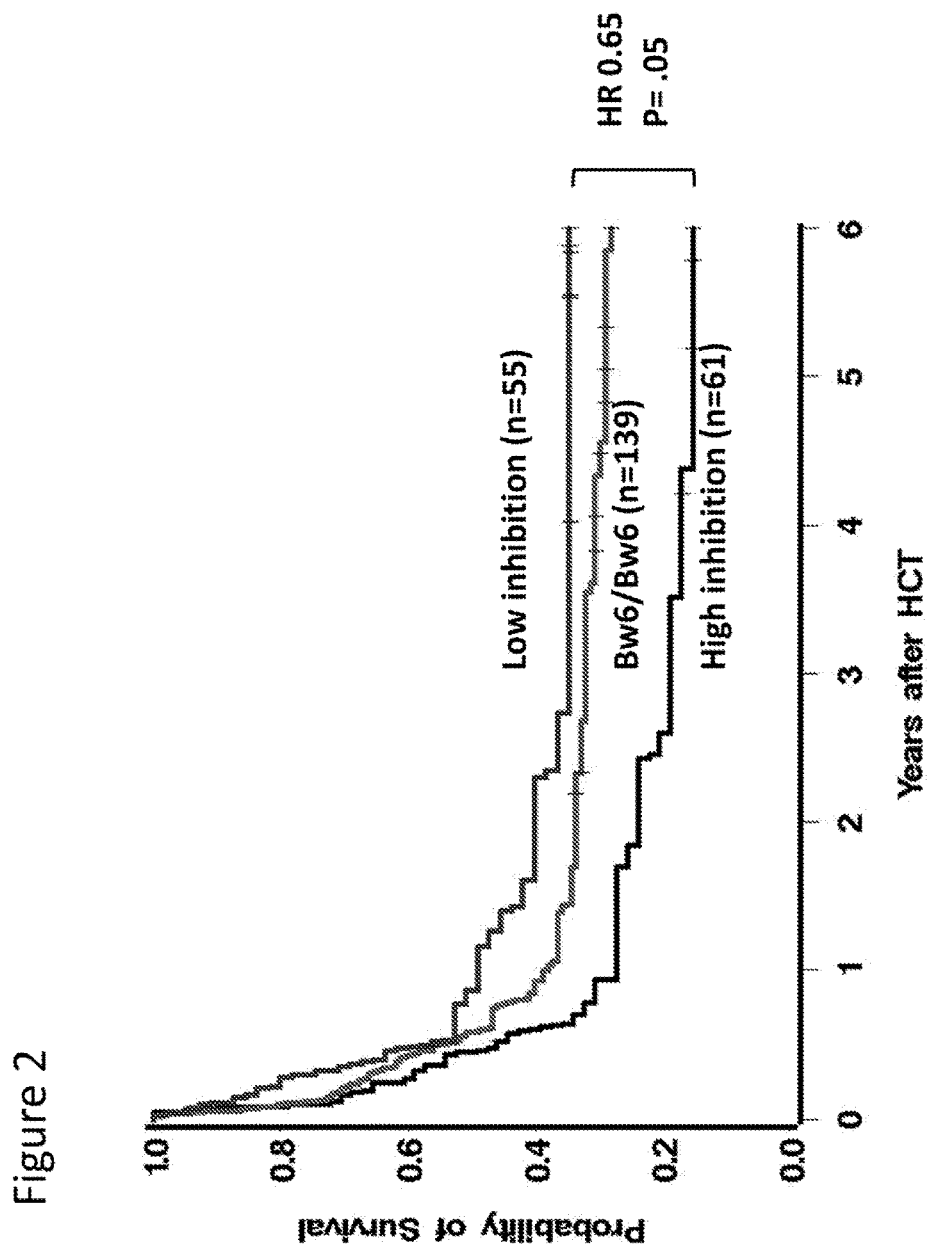
FIG. 2. Strength of KIR3DL1 inhibition is associated with mortality in AML patients following HCT. Weak inhibitory subtype combinations (3DL1-H+Bw4-T$^{80}$ (not including B*2705) and 3DL1-L+Bw4-P) are associated with lower mortality compared to strong inhibitory combinations (3DL1-H+Bw4-I$^{80}$, 3DL1-H+B*2705, and 3DL1-L+non-B*2705Bw4-I$^{80}$). Bw6 homozygous donors are associated with intermediate protection from mortality.

Strength of NK Inhibition is Associated with AML Relapse and Mortality after HCT Consistent findings among the donor 3DL1-H and 3DL1-L subtype groups, where strong and weak inhibitory interactions with Bw4 subtypes led to higher and lower relapse respectively, permitted combination of the two groups. Among the combined groups, weak inhibitory subtype combinations (KIR3DL1-L+Bw4-$I^{80}$ and KIR3DL1-H+Bw4-$T^{80}$), were strongly associated with lower relapse in AML patients compared to the strong inhibitory combinations (3DL1-L+Bw4-$T^{80}$, and 3DL1-H+Bw4-$I^{80}$) (HR 0.46; P=0.02; FIG. 1a, Table 2), and even more striking when compared to the strongly inhibitory combinations of 3DL1-H+B*57 or +B*2705 (HR 0.3; P=0.006; FIG. 1b, Table 2). Correspondingly, there was lower mortality among patients transplanted from donors with weak or non-inhibitory combinations compared to patients transplanted from donors with strong inhibitory combinations (HR 0.65; P=0.05; FIG. 2). Moreover, distribution of KIR haplotype-A homozygosity, an unfavorable KIR genotype, was equivalent between donors with high inhibitory combinations (21%) and low inhibitory combinations (22%).

Figure 3:
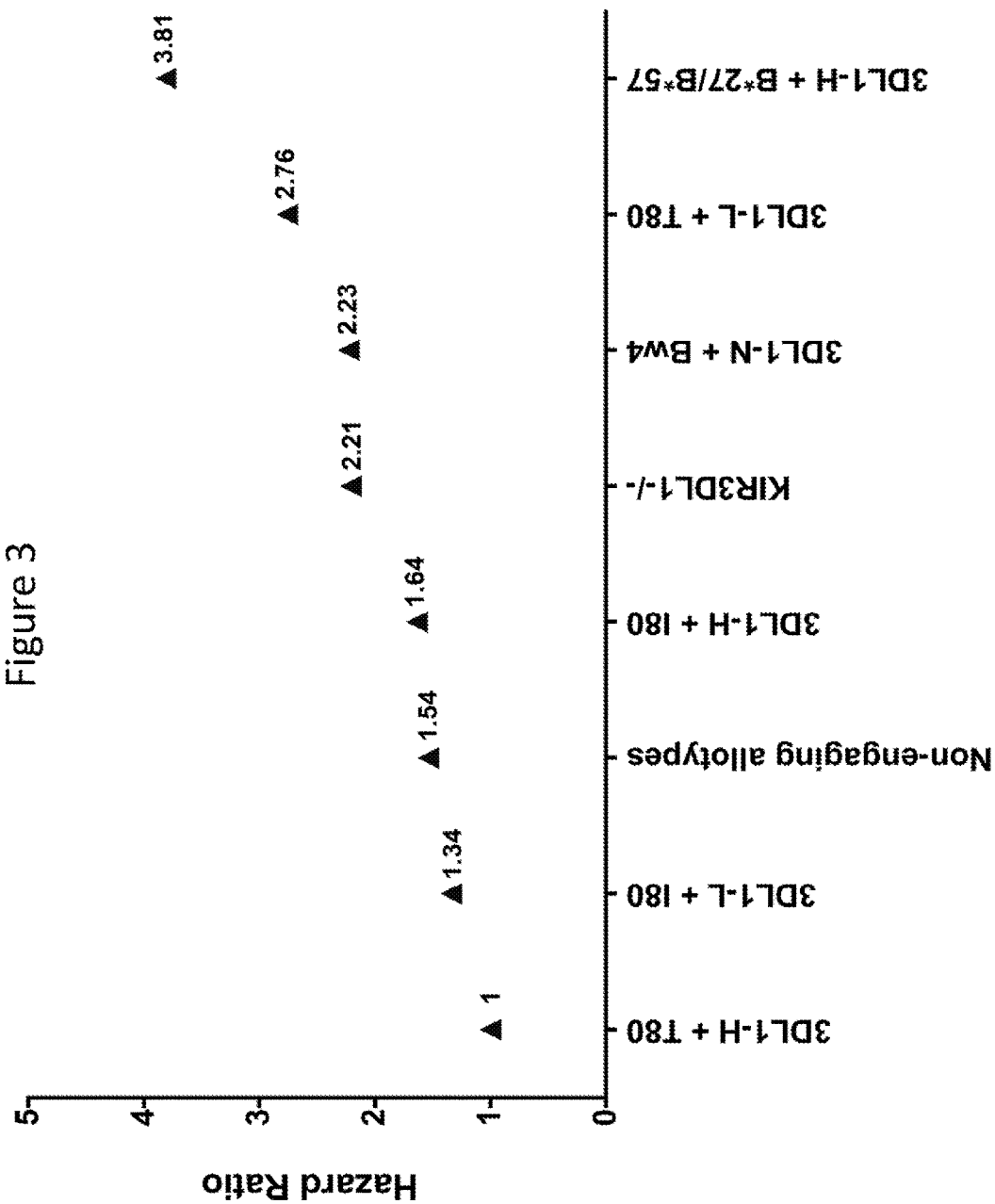
FIG. 3. KIR3DL1+HLA-B allele combinations define a hierarchy of protection from AML relapse following allogeneic HCT. Donor allotype pairs are arranged by relative hazard ratios for AML relapse after HCT.

From these analyses, a hierarchy of protection from AML relapse is identified, ranging from the highly protective weakly inhibitory KIR3DL1/Bw4 allotype combinations to the intermediate protective effect of Bw6/Bw6 to the strongly inhibitory KIR3DL1/Bw4 subtype combinations associated with susceptibility and, in the case of the Bw4-I80 B*2705 and B*57 alleles, "super-susceptibility," to relapse (FIG. 3). In contrast to relapse and survival, there was no statistically significant association between subtype combinations and graft-versus-host disease (data not shown).

HLA-A Alleles Bearing the Bw4-$I^{80}$ Epitope do not Influence AML Relapse

Some HLA-A allotypes exhibit the Bw4-$I^{80}$ epitope, binding weakly and variably to KIR3DL1[14,32-34]. When donors with HLA-A alleles containing the Bw4-$I^{80}$ epitope were included with HLA-B alleles in the analysis, there was no added effect on relapse (data not shown), suggesting that interaction between KIR3DL1 and the Bw4 epitope presented by HLA-A subtypes may not play as significant a role in NK education and leukemic surveillance following HCT as the HLA-B Bw4 subtypes.

Donor KIR3DL1-N and HLA-Bw4 Combinations are not Associated with HCT Outcomes

Studies in HIV-infected individuals identified an association between combinations of 3DL1-N and Bw4 subtypes with improved HIV control, although the biological mechanism is unclear[20]. AML patients transplanted from donors with 3DL1-N in aggregate experienced a higher relapse rate compared to the most favorable low-affinity combination 3DL1-H+Bw4-$T^{80}$ (HR 2.2, FIG. 3). There were no statistically significant differences in outcome in this cohort for AML patients transplanted from donors with specific combinations of 3DL1-N with Bw4-$I^{80}$, Bw4-$T^{80}$ or Bw6/Bw6 (data not shown).

Materials and Methods

Patients, Donors and Transplant Characteristics

We evaluated 299 patients who received an allogeneic hematopoietic stem allograft from an unrelated donor (URD) following myeloablative conditioning as treatment for a myeloid malignancy (AML 70.2%, CML 6.3%, MDS 23.5%). All transplants were facilitated by the National Marrow Donor Program (NMDP) between 1995 and 2002. Clinical data, HLA allele typing, KIR3DL1 allele typing, and donor cell lines or donor genomic DNA for KIR genotyping were provided by the Center for International Blood and Marrow Transplant Research (CIBMTR). The CIBMTR is a research affiliation of the International Bone Marrow Transplant Registry, Autologous Blood and Marrow Transplant Registry, and the National Marrow Donor Program (NMDP), comprising a group of more than 450 centers worldwide that contribute hematopoietic stem cell transplant data to the Statistical Center at the Medical College of Wisconsin in Milwaukee and the NMDP Coordinating Center in Minneapolis, Minn. Patients were followed longitudinally, with yearly follow-up. Studies conducted by the CIBMTR were performed in compliance with the Privacy Rule (HIPAA) as a Public Health Authority, and in compliance with federal regulations pertaining to the protection of human research participants as determined by the Institutional Review Boards of the NMDP and the Medical College of Wisconsin. 236 patients (78.9%) received an allograft from an unrelated donor matched at 10 of 10 possible HLA alleles, and 63 (21.1%) received and URD allograft matched at 9 of 10 alleles. 283 donor-recipient pairs (94.6%) were matched for both HLA-B alleles, with the remaining 16 pairs mismatched for one HLA-B allele. Only 3 patients (1.0%) were HLA-B epitope/KIR3DL1 ligand mismatched with their donors. A total of 257 (85.9%) allografts were T-cell replete, and 268 (95.7%) were of marrow origin. All patients received an ablative conditioning regimen. Cyclosporine and methotrexate were used as GVHD prophylaxis in 252 (84.3%) patients; 5 patients received tacrolimus-based GVHD prophylaxis. The 42 (14.0%) patients who received a T-cell depleted transplant did not receive additional GVHD prophylaxis.

HLA and KIR3DL1 Allele Typing

High-resolution HLA genotyping (HLA-A, B, C, DRB1 and DQB1) of patients and donors was obtained from CIBMTR. Typing for donor KIR gene presence/absence was performed using previously described methods[47] or by Invitrogen KIR genotyping kit as per manufacturer's instructions. KIR3DL1 allele level typing was executed using PCR-based methods and sequencing, as previously described[48-51]. All KIR3DL1 alleles were verified by sequencing. All samples were typed for KIR3DL1 alleles independently in two different laboratories, with any discrepancies resolved by a third independent laboratory.

HLA and KIR3DL1 subtype grouping

KIR3DL1 alleles were divided into high-, low- and null-expressing groups based on published data[14,16-18]. Specifically, the high-expressing alleles (KIR3DL1-h) present in this patient cohort included KIR3DL1*001, *002, *008, *020, *015, *033 and *052; the low-expressing alleles (KIR3DL1-l) were *005, *007, and *053. The KIR3DL1 allele *004 was considered as a non-expressed allele (KIR3DL1-n). To investigate the different effects of high- versus low-expressing subtype combinations, donors were segregated similar to published grouping criteria[20]: donors with only KIR3DL1-h alleles (KIR3DL1*h/*h; KIR3DL1*h/3DS1; grouped as KIR3DL1-H) were segregated from those with at least one KIR3DL1-l allele (KIR3DL1*l/*l, KIR3DL1*l/*h, KIR3DL1*l/3DS1; grouped as KIR3DL1-L). Considering the different biological role of the intracellularly sequestered KIR3DL1*004 null allele, donors with at least one *004 allele (3DL1*n/*n, 3DL1*n/*h, 3DL1*n/*l, 3DL1*n/3DS1; grouped as 3DL1-N) were also evaluated separately. Donors were considered Bw4-$I^{80}$, Bw4-$T^{80}$, or Bw4-negative (Bw6/Bw6). All donors positive for Bw4-$I^{80}$, homozygous or heterozygous, were considered in the Bw4-$I^{80}$ group, independent of the presence/absence of HLA-Bw4-$T^{80}$.

Statistical Analysis

Subtype combinations of KIR3DL1 and HLA-Bw4 were compared using Cox regression for the time-to-event outcomes relapse and overall mortality. Variables included age, disease severity, degree of HLA-matching, type of disease (AML versus MDS/CML, where appropriate), type of transplant (T-cell deplete versus T-cell replete), and presence of KIR3DS1 (the group assignments did not remove 3DS1). Due to relatively limited numbers of events for some comparisons (particularly for relapse among KIR3DL1 subgroups), the ability to adjust for non-KIR/HLA variables was limited; in some cases, at most one additional variable was included in the regression model, with each variable included sequentially. Estimates of the probability of overall survival were obtained using the method of Kaplan and Meier, and estimates of the probability of relapse were summarized using cumulative incidence estimates, where death without relapse was regarded as a competing risk for relapse.

TABLE 1

| Transplant characteristics | AML |
|---|---|
| Number of patients | 299 |
| Median age, y | 39.3 |
| (range) | (1.8-68.9) |
| Disease Status at transplant* | |
| Early | 89 (29.8) |
| Intermediate | 84 (28.1) |
| Advanced | 126 (42.1) |
| Other MDS | |
| HLA match | |
| 10/10 | 236 (78.9) |
| 9/10 | 63 (21.1) |
| 8/10 | 0 |

TABLE 1-continued

| Transplant characteristics | AML |
|---|---|
| HLA-B match | |
| 2/2 | 283 (94.7) |
| 1/2 | 16 (5.3) |
| HLA-B subtype match[Ω] | 296 (99.0) |
| HLA-B subtype mismatch | 3 (1.0) |
| Patient Bw4-$I^{80}$ →Donor Bw4-$T^{80}$ | 1 |
| Patient Bw4-$T^{80}$ →Donor Bw4-$I^{80}$ | 1 |
| Patient Bw6/Bw6→Donor Bw4-$I^{80}$ | 1 |
| Transplant Type | |
| Ablative | 299 (100) |
| T-deplete | 42 (14.0) |
| T-replete | 257 (85.9) |
| Graft type | |
| Bone marrow | 268 (89.6) |
| Peripheral blood stem cells | 31 (10.4) |
| GVHD prophylaxis | |
| Cyclosporine A + Methotrexate | 252 (84.3) |
| Non-Cyclosporine A | 5 (1.7) |
| T-cell depletion | 42 (14.0) |
| Donor KIR3DL1 allotype | 284 (95.0) |
| Donor KIR3DL1-h positive | 205 (68.6) |
| Donor KIR3DL1-l positive | 80 (26.8) |
| Donor KIR3DL1-n positive | 83 (27.8) |
| Donor KIR3DS1-positive | 115 (38.5) |
| Donor KIR3DL1 subtype groups | |
| Donor KIR3DL1-H | 130 (45.8) |
| Donor KIR3DL1-L | 69 (24.3) |
| Donor KIR3DL1-N | 82 (28.9) |
| Not assessable# | 3 (1.0) |
| Donor HLA-B subtype groups | |
| Bw6 homozygous | 123 (41.1) |
| Bw4-$I^{80}$ | 86 (28.8) |
| Bw4-$T^{80}$ | 90 (30.1) |

Values are n (%) unless otherwise noted.

* Disease status was defined as follows. AML: "early" for first complete remission, "intermediate" for second complete remission or higher complete remission, and "advanced" for primary induction failure, first relapse, second or higher relapse.

Ω HLA-B subtype match or mismatch is defined as presence or absence of a different HLA-B subtype in the patient and donor, where HLA-B subtypes are defined as HLA-Bw6, HLA-Bw4-$I^{80}$, or HLA-Bw4-$T^{80}$.

KIR3DL1 alleles not classifiable as high, low or null as described in "METHODS", based on available literature.

AML, acute myeloid leukemia; CML, chronic myeloid leukemia; MDS, myelodysplastic syndrome; GVHD, graft versus host disease.

TABLE 2

Subtype combinations of KIR3DL1 and HLA-B and relapse after HCT for AML, adjusted results

| KIR3DL1 + HLA-B* subtype | Hazard Ratio | 95% CI | P-value |
|---|---|---|---|
| Extra-high: 3DL1-H + B*57 or 3DL1-H + B*2705 | 1 | — | — |
| High: 3DL1-H + Bw4-$I^{80}$ (non-*B57) or 3DL1-L + Bw4-$T^{80}$ (non-B*2705) | 0.54 | 0.24-1.21 | .13 |
| No Bw4: 3DL1-H + Bw6/Bw6 or 3DL1-L + Bw6/Bw6 | 0.4 | 0.19-0.83 | .014 |
| Low: 3DL1-H + Bw4-$T^{80}$ or 3DL1-L + Bw4-$I^{80}$ | 0.3 | 0.13-0.7 | .006 |

*"Extra-high", "high", and low" refer to strength of inhibition

REFERENCES

1. Parham, P. MHC class I molecules and KIRs in human history, health and survival. *Nat Rev Immunol* 5, 201-214 (2005).
2. Kim, S. et al. Licensing of natural killer cells by host major histocompatibility complex class I molecules. *Nature* 436, 709-13 (2005).
3. Anfossi, N. et al. Human NK cell education by inhibitory receptors for MHC class I. *Immunity* 25, 331-42 (2006).
4. Yu, J. et al. Hierarchy of the human natural killer cell response is determined by class and quantity of inhibitory receptors for self-HLA-B and HLA-C ligands. *J Immunol* 179, 5977-89 (2007).
5. Fernandez, N. et al. A subset of natural killer cells achieves self-tolerance without expressing inhibitory receptors specific for self-MHC molecules. *Blood* 105, 4416-4423 (2005).
6. Yokoyama, W. & Kim, S. Licensing of natural killer cells by self-major histocompatibility complex class I. *Immunol Rev* 214, 143-154 (2006).
7. Hsu, K. et al. Improved outcome in allogeneic hematopoietic stem cell transplantation in acute myelogenous leukemia (AML) predicted by donor KIR genotype and recipient HLA genotype in T-cell depleted HLA-identical sibling transplants. *Blood* 105, 4878-4884 (2005).
8. Yu, J. et al. Breaking tolerance to self, circulating natural killer cells expressing inhibitory KIR for non-self HLA exhibit effector function after T cell-depleted allogeneic hematopoietic cell transplantation. *Blood* 113, 3875-84 (2009).
9. Miller, J. et al. Missing KIR-ligands is associated with less relapse and increased graft versus host disease (GVHD) following unrelated donor allogeneic HCT. *Blood* 109, 5058-5061 (2007).
10. Parham, P., Norman, P. J., Abi-Rached, L. & Guethlein, L. Variable NK cell receptors exemplified by human KIR3DL1/S1. *J Immunol* 187, 11-19 (2011).
11. Gillespie, G. et al. Lack of KIR3DS1 binding to MHC class I Bw4 tetramers in complex with CD8+ T cell epitopes. *AIDS Res Hum Retroviruses* 23, 451-455 (2007).
12. O'Connor, G. et al. Functional polymorphism of the KIR3DL1/S1 receptor on human NK cells. *J Immunol* 178, 235-241 (2007).
13. Vivian, J. P. et al. Killer cell immunoglobulin-like receptor 3DL1-mediated recognition of human leukocyte antigen B. *Nature* 479, 401-5 (2011).
14. Yawata, M. et al. Roles for HLA and KIR polymorphisms in natural killer cell repertoire selection and modulation of effector function. *J Exp Med* 203, 633-645 (2006).
15. Can, W., Pando, M. & Parham, P. KIR3DL1 polymorphisms that affect NK cell inhibition by HLA-Bw4 ligand. *J Immunol* 175, 5222-5229 (2005).
16. Thomas, R. et al. Novel KIR3DL1 alleles and their expression levels on NK cells: convergent evolution of KIR3DL1 phenotype variation? *J Immunol* 180, 6743-6750 (2008).
17. Pando, M. J., Gardiner, C. M., Gleimer, M., McQueen, K. L. & P. Parham. The protein made from a common allele of KIR3DL1 (3DL1*004) is poorly expressed at cell surfaces due to substitution at positions 86 in Ig domain 0 and 182 in Ig domain 1. *J Immunol* 171, 6640-6649 (2003).
18. Gardiner, C. M. et al. Different NK cell surface phenotypes defined by the DX9 antibody are due to KIR3DL1 gene polymorphism. *J Immunol* 166, 2992-3001 (2001).
19. Boulet, S. et al. HIV protective KIR3DL1 and HLA-B genotypes influence NK cell function following stimulation with HLA-devoid cells. *J Immunol* 184, 2057-2064 (2010).
20. Martin, M. et al. Innate partnership of HLA-B and KIR3DL1 subtypes against HIV-1. *Nat Genet* 39, 733-740 (2007).
21. Martin, M. P. et al. Epistatic interaction between KIR3DS1 and HLA-B delays the progression to AIDS. *Nature Genetics* 31, 429-434 (2002).
22. Alter, G. et al. Differential natural killer cell-mediated inhibition of HIV-1 replication based on distinct KIR/HLA subtypes. *J Exp Med* 204, 3027-3036 (2007).
23. Kamya, P. et al. Receptor-ligand requirements for increased NK cell polyfunctional potential in slow progressors infected with HIV-1 coexpressing KIR3DL1*h/*y and HLA-B*57. *J Virol* 85, 5949-5960 (2011).
24. Schwartz, O., Marechal, V., Le Gall, S., Lemonnier, F. & Heard, J. Endocytosis of major histocompatibility complex class I molecules is induced by the HIV-1 Nef protein. *Nat Med* 2, 338-342 (1996).
25. Wetzler, M. et al. HLA class I antigen cell surface expression is preserved on acute myeloid leukemia blasts at diagnosis and at relapse. *Leukemia* 15, 128-133 (2001).
26. Ruggeri, L. et al. Donor natural killer cell allorecognition of missing self in haploidentical hematopoietic transplantation for acute myeloid leukemia: challenging its predictive value. *Blood* 110, 433-440 (2007).
27. Venstrom, J. et al. HLA-C-dependent prevention of leukemia relapse by donor activating KIR2DS1. *New England Journal of Medicine* 367, 805-816 (2012).
28. Cooley, S. et al. Donors with group B haplotypes improve relapse-free survival after unrelated hemaotpoietic transplantation for acute myeloid leukemia. *Blood* 113, 726-732 (2009).

29. Hsu, K. et al. KIR ligands and prediction of relapse after unrelated donor hematopoietic cell transplantation for hematologic malignancy. *Biol Blood Mar Transpl* 12, 828-836 (2006).
30. Hollenbach, J. A. et al. Report from the killer immunoglobulin-like receptor (KIR) anthropology component of the 15th International Histocompatibility Workshop: worldwide variation in the KIR loci and further evidence for the co-evolution of KIR and HLA. *Tissue Antigens* 76, 9-17 (2010).
31. Carrington, M. & O'Brien, S. The influence of HLA genotype on AIDS. *Annu Rev Med* 54, 535-551 (2003).
32. Stern, M., L Ruggeri, L., Capanni, M., Mancusi, A. & Velardi, A. Human leukocyte antigens A23, A24 and A32 but not A25 are ligands for KIR3DL1. *Blood* 112, 708-710 (2008).
33. Foley, B. et al. The reactivity of Bw4+HLA-B and HLA-A alleles with KIR3DL1: implications for patient and donor suitability for haploidentical stem cell transplantations. *Blood* 112, 435-443 (2008).
34. Gumperz, J., Litwin, V., Phillips, J., Lanier, L. & Parham, P. The Bw4 public epitope of HLA-B molecules confers reactivity with NK cell clones that express NKB1, a putative HLA receptor. *J Exp Med* 181, 1133-1144 (1995).
35. Ruggeri, L. et al. Role of natural killer cell alloreactivity in HLA-mismatched hematopoietic stem cell transplantation. *Blood* 94, 333-339 (1999).
36. Lee, S. J. et al. High-resolution donor-recipient HLA matching contributes to the success of unrelated donor marrow transplantation. *Blood* 110, 4576-4583 (2007).
37. Petersdorf, E. W. et al. Major-histocompatibility-complex class I alleles and antigens in hematopoietic-cell transplantation. *N Engl J Med* 345, 1794-800 (2001).
38. Ruggeri, L. et al. Effectiveness of donor natural killer cell alloreactivity in mismatched hematopoietic transplants. *Science* 295, 2097-100 (2002).
39. Giebel, S. et al. Survival advantage with KIR ligand incompatibility in hematopoietic stem cell transplantation from unrelated donors. *Blood* 102, 814-9 (2003).
40. Cooley, S. et al. Donor selection for natural killer cell receptor genes leads to superior survival after unrelated transplantation for acute myelogenous leukemia. *Blood* 116, 2411-2419 (2010).
41. Hsu, K. C., Chida, S., Geraghty, D. & Dupont, B. The killer cell immunoglobulin-like receptor (KIR) genomic region: gene-order, haplotypes and allelic polymorphism. *Immunol Rev* 190, 40-52 (2002).
42. Venstrom, J. M. et al. KIR and HLA genotypes are associated with disease progression and survival following autologous hematopoietic stem cell transplantation for high-risk neuroblastoma. *Clin Cancer Res* 15, 7330-4 (2009).
43. Tarek, N. et al. Unlicensed natural killer cells target neuroblastoma following anti-GD2 antibody treatment. *J Clin Invest* 122, 3260-3270 (2012).
44. Thananchai, H. et al. Cutting edge: allele-specific and peptide-dependent interactions between KIR3DL1 and HLA-A and HLA-B. *J Immunol* 178, 33-37 (2007).
45. Vivian, F. et al. Killer cell immunoglobulin-like receptor 3DL1-mediated recognition of human leukocyte antigen B. *Nature* 479, 401-406 (2011).
46. Single, R. et al. Global diversity and evidence for coevolution of KIR and HLA. *Nat Genet* 39, 1114-9 (2007).
47. Hsu, K. C. et al. Killer Ig-like receptor haplotype analysis by gene content: evidence for genomic diversity with a minimum of six basic framework haplotypes, each with multiple subsets. *J Immunol* 169, 5118-29 (2002).
48. Belle, I. et al. Investigation of killer cell immunoglobulin-like receptor gene diversity in KIR3DL1 and KIR3DS1 in a transplant population. *Tissue Antigens* 71, 434-439 (2008).
49. Lebedeva, T., Ohashi, M., Zannelli, G., Cullen, R. & Yu, N. Comprehensive approach to high-resolution KIR typing. *Hum Immunol* 68, 789-796 (2007).
50. Levinson, R. et al. Combination of KIR and HLA gene variants augments the risk of developing birdshot chorioretinopathy in HLA-A*29-positive individuals. *Genes Immun* 9, 249-258 (2008).
51. Jiang, B., Hou, L., Chen, M., Ng, J. & Hurley, C. The profile of KIR3DL1 and KIR3DS1 alleles in an African American population resembles that found in African populations. *Tissue Antigens* 76, 64-66 (2010).

What is claimed is:

1. A method for protecting an acute myelogenous leukemia (AML) patient recipient from leukemic relapse following allogeneic hematopoietic cell transplantation (HCT), wherein the patient recipient expresses HLA-B genotype HLA-Bw4-$I^{80}$, the method comprising:
    (a) detecting the presence of HLA-B genotype HLA-Bw4-$I^{80}$ in a candidate donor sample obtained from a candidate donor,
    (b) detecting the presence of a KIR3DL1 genotype selected from the group consisting of KIR3DL1*l/*l, KIR3DL1*l/*h, and KIR3DL1*l/KIR3DS1, in the candidate donor sample of step (a);
        (i) wherein KIR3DL1*h is a KIR3DL1 allele selected from the group consisting of KIR3DL1 *001, *002, *008, *015, *020, *033, and *052,
        (ii) wherein KIR3DL1*l is a KIR3DL1 allele selected from the group consisting of KIR3DL1*005, *007, and *053;
        (iii) wherein the presence of HLA-Bw4-$I^{80}$ and the KIR3DL1 genotype in the candidate donor sample indicates an allele combination of HLA-Bw4-$I^{80}$ and the KIR3DL1 genotype; and
    (c) administering to the patient recipient an allogeneic hematopoietic graft derived from the candidate donor expressing the allele combination of HLA-Bw4-$I^{80}$ and the KIR3DL1 genotype,
    wherein HLA-Bw4-$I^{80}$ is a HLA-Bw4 genotype of Bw4-$I^{80}$/Bw4-$I^{80}$, Bw4-$I^{80}$/Bw6, or Bw4-$I^{80}$/Bw4-$T^{80}$.
2. The method of claim 1, wherein the allele combination of HLA-Bw4-$I^{80}$ and the KIR3DL1 genotype is detected by assaying the candidate donor sample, wherein the candidate donor sample comprises genomic nucleic acids derived from blood, blood fractions, peripheral blood cells, skin or tissue biopsies, buccal swabs or umbilical cord blood.
3. The method of claim 2, wherein maternal and paternal KIR3DL1 alleles in the candidate donor sample are detected via sequence-specific oligonucleotide hybridization, sequencing, PCR-SSP, or any combination thereof.
4. The method of claim 1, wherein KIR3DS1 is a KIR3DS1 allele selected from the group consisting of KIR3DS1*013, *047, *010, *011, *012, *014, *045, *046, *048, *049N, *050, *055, and *058.
5. The method of claim 1, wherein the allogeneic hematopoietic graft is a bone marrow graft or a peripheral bone stem cell graft.
6. The method of claim 1, wherein the hematopoietic cell transplantation is ablative, T-cell depleted, or T-cell replete.

7. The method of claim 1, wherein the AML, patient recipient is at the early, intermediate or advanced stage of AML.

8. The method of claim 1, wherein the patient recipient does not suffer from GVHD after the allogeneic hematopoietic cell transplantation.

9. A method for protecting an acute myelogenous leukemia (AML) patient recipient from leukemic relapse following allogeneic hematopoietic cell transplantation (HCT), wherein the patient recipient expresses HLA-B genotype HLA-Bw4-$T^{80}$, the method comprising:
   (a) detecting the presence of HLA-B genotype HLA-Bw4-$T^{80}$ in a candidate donor sample obtained from a candidate donor;
   (b) detecting the presence of a KIR3DL1 genotype selected from the group consisting of KIR3DL1*h/*h, and KIR3DL1*h/KIR3DS1, in the candidate donor sample of step (a);
      (i) wherein KIR3DL1*h is a KIR3DL1 allele selected from the group consisting of KIR3DL1 *001, *002, *008, *015, *020, *033, and *052;
      (ii) wherein the presence of HLA-Bw4-$T^{80}$ and the KIR3DL1 genotype in the candidate donor sample indicates an allele combination of HLA-Bw4-$T^{80}$ and the KIR3DL1 genotype; and
   (c) administering to the patient recipient an allogeneic hematopoietic graft derived from the candidate donor expressing the allele combination of HLA-Bw4-$T^{80}$ and the KIR3DL1 genotype ,
   wherein HLA-Bw4-$T^{80}$ is a HLA-Bw4 genotype of Bw4-$T^{80}$/Bw4-$T^{80}$ or Bw4-$T^{80}$/Bw6; and
   wherein the HLA-Bw4-$T^{80}$ genotype of the candidate donor does not comprise B*2705.

10. The method of claim 9, wherein the allele combination of HLA-Bw4-$T^{80}$ and the KIR3DL1 genotype is detected by assaying the candidate donor sample, wherein the candidate donor sample comprises genomic nucleic acids derived from blood, blood fractions, peripheral blood cells, skin or tissue biopsies, buccal swabs or umbilical cord blood.

11. The method of claim 10, wherein maternal and paternal KIR3DL1 alleles in the candidate donor sample are detected via sequence-specific oligonucleotide hybridization, sequencing, PCR-SSP, or any combination thereof.

12. The method of claim 9, wherein KIR3DS1 is a KIR3DS1 allele selected from the group consisting of KIR3DS1*013, *047, *010, *011, *012, *014, *045, *046, *048, *049N, *050, *055, and *058.

13. The method of claim 9, wherein the allogeneic hematopoietic graft is a bone marrow graft or a peripheral bone stem cell graft.

14. The method of claim 9, wherein the hematopoietic cell transplantation is ablative, T-cell depleted, or T-cell replete.

15. The method of claim 9, wherein the AML, patient recipient is at the early, intermediate or advanced stage of AML.

16. The method of claim 9, wherein the patient recipient does not suffer from GVHD after the allogeneic hematopoietic cell transplantation.

* * * * *